United States Patent [19]

Cline et al.

[11] Patent Number: 5,187,658

[45] Date of Patent: Feb. 16, 1993

[54] SYSTEM AND METHOD FOR SEGMENTING INTERNAL STRUCTURES CONTAINED WITHIN THE INTERIOR REGION OF A SOLID OBJECT

[75] Inventors: Harvey E. Cline, Schenectady; William E. Lorensen, Ballston Lake, both of N.Y.

[73] Assignee: General Electric Company, Schenectady, N.Y.

[21] Appl. No.: 466,526

[22] Filed: Jan. 17, 1990

[51] Int. Cl.$^5$ ............................................. G06F 15/42
[52] U.S. Cl. ............................... 364/413.13; 395/129; 340/727; 324/306
[58] Field of Search .......................... 364/413.13, 555; 395/600, 124, 135, 125; 128/653 A; 324/309

[56] References Cited

U.S. PATENT DOCUMENTS

| | | | |
|---|---|---|---|
| 4,468,761 | 8/1984 | Rietsch | 367/43 |
| 4,471,306 | 9/1984 | Edelstein et al. | 324/309 |
| 4,710,876 | 12/1987 | Cline et al. | 364/414 |
| 4,719,585 | 1/1988 | Cline et al. | 364/518 |
| 4,729,098 | 3/1988 | Cline et al. | 364/414 |
| 4,732,157 | 3/1988 | Kaplan et al. | 128/696 |
| 4,751,643 | 6/1988 | Lorensen et al. | 364/414 |
| 4,791,567 | 12/1988 | Cline et al. | 364/413.13 |
| 4,821,213 | 4/1989 | Cline et al. | 364/522 |
| 4,830,012 | 5/1989 | Riederer | 128/653 |
| 5,051,903 | 9/1991 | Pela et al. | 364/413.13 |

OTHER PUBLICATIONS

H. E. Cline et al., "Two Algorithms for the Three-Dimensional Reconstruction of Tomograms", *Medical Physics*, 15(3), pp. 320-327, May/Jun. 1988.

H. E. Cline et al., "Vascular Morphology by Three-Dimensional Magnetic Resonance Imaging", *Magnetic Resonance Imaging*, vol. 7, pp. 45-54, Nov. 1, 1989.

*Primary Examiner*—Gary V. Harkcom
*Assistant Examiner*—Michael S. Smith
*Attorney, Agent, or Firm*—Lawrence P. Zale; Marvin Snyder

[57] ABSTRACT

In order to display the surfaces of internal structures within a solid body from non-intrusively acquired data sets, it is useful to segment the data sets into the internal structures of interest before searching for the surfaces of such structures. To accomplish this, a data segmentation system uses a plurality of sample data points to construct a statistical probability distribution for a plurality of internal structures. Using these probability distributions, each data point is labeled with the most likely structure identification. Searching the thus-segmented data points for surfaces is considerably faster than is possible with the entire data set and produces surface renditions with fewer anomalies and errors. If the solid body is a human head, and nuclear magnetic resonance (NMR) is used to obtain two data sets corresponding to the two NMR echoes, then the probability distribution is bivariate and the two echoes can be plotted against each other to assist in identifying tissue clusters.

12 Claims, 4 Drawing Sheets

DATA SEGMENTATION SYSTEM

DATA SEGMENTATION PROCESS

TISSUE PROBABILITY DISTRIBUTION

DATA SAMPLE SCATTER PLOT

DATA DISPLAY SYSTEM

SYSTEM AND METHOD FOR SEGMENTING INTERNAL STRUCTURES CONTAINED WITHIN THE INTERIOR REGION OF A SOLID OBJECT

TECHNICAL FIELD

This invention relates to systems for displaying surfaces of internal structures within solid bodies, and, more particularly, to systems for detecting and displaying a plurality of such surfaces with similar physical properties.

BACKGROUND OF THE INVENTION

It is well known to obtain three-dimensional arrays of data representing one or more physical properties at regular grid positions within the interior of solid bodies. Such data can be obtained by non-intrusive methods such as computed axial tomographic (CAT) x-ray scanning systems, by nuclear magnetic resonance (NMR) imaging systems, or by other non-intrusive mechanisms such as ultrasound, positron emission tomography (PET), emission computed tomography (ECT) and multimodality imaging (MMI). Each of these techniques produces a planar, grid-like array of values for each of a succession of slices of the solid object, thus providing a three-dimensional array of such values. Typically, the solid object is a human body or a portion thereof, although the method is equally applicable to other natural or artificial bodies. In the case of CAT scanning, the physical value is the coefficient of x-ray absorption. For NMR imaging, the physical values are the spin-spin and the spin-lattice relaxation echoes. In any event, the measured physical values reflect the variations in composition, density or surface characteristics of the underlying physical structures.

It is likewise known to utilize such three-dimensional arrays of interior physical values to generate visual images of the interior structures within the body. In the case of the human body, the visual images thus produced can be used for medical purposes such as diagnostics or for the planning of surgical procedures In order to display two-dimensional images of such three-dimensional interior structures, however, it is necessary to locate the position of the surface of such structure within the array of physical values. This has been accomplished in the prior art by comparing the array values to a single threshold value, or to a range of threshold values, corresponding to the physical property values associated with that surface. Bones or any other tissue, for example, can be characterized by a known range of density values to which the array values can be compared. Once the surface location is determined, this surface must be shaded so as to give the human eye the correct impression of the shape and disposition of that surface when it is displayed on a two-dimensional display device. To provide such shading, the angular direction of a vector normal or orthogonal to the surface at each point on the surface is compared to the viewing angle of the observer. The intensity of shading can then be adjusted so as to be proportional to the difference between these angles. Normal vectors with components directed away from the viewing angle can be ignored since the associated surfaces are hidden from view.

It is thus known to use a single array of values of a physical property within the interior of a solid body to generate perspective images of arbitrarily selected internal structures within the body, seen as if viewed from arbitrarily chosen viewing angles, all by manipulating the selfsame single array of values. Techniques for displaying such internal structures of a solid body from non-intrusive three-dimensional data arrays are taught in H. E. Cline et al. U.S. Pat. No. 4,710,876, granted Dec. 1, 1987, H. E. Cline et al. U.S. Pat. No. 4,719,585 granted Jan. 12, 1988, H. E. Cline et al. U.S. Pat. No. 4,729,098, granted Mar. 1, 1988, W. E. Lorensen et al. U.S. Pat. No. 4,751,643, granted June 14, 1988, H. E. Cline et al. U.S. Pat. No. 4,791,567, granted Dec. 13, 1988, U.S. Pat. No. 4,821,213, granted Apr. 11, 1989, U.S. Pat. No. 4,879,668, U.S. Pat. No. 4,985,834, and U.S. Pat. No. 4984,157 all of which are assigned to applicants' assignee, and the following copending application of H. E. Cline et al. assigned to applicants' assignee: Ser. No. 282,666, filed Dec. 12, 1988, now abandoned. All of these display techniques, however, require that the three-dimensional data be segmented into data subsets representing a single one, or a plurality, of integral internal structures. Such data subsets can then be processed to smooth the depicted surfaces, to provide color for distinguishing different structures, and to provide surface gradient shading to enhance three-dimensional displays.

CAT scanning produces x-ray absorption values with which threshold values are suitable for distinguishing between data representing different structures with substantially different properties, such as bones and surrounding soft tissues. It is difficult, however, using CAT scan values, to distinguish between adjacent tissues with similar physical characteristics, such as is found in the human head where different tissues result in overlapping intensity ranges. Closely adjacent and intermingled tissues with the same or closely similar values of the scanned physical property, for example, are difficult or impossible to discriminate. Attempts to image such tissues result in an image that includes multiple tissues with inadequate or concealed details. This problem is discussed in "3D Reconstruction of the Brain from Magnetic Resonance Images Using a Connectivity Algorithm," by H. E. Cline et al., *Magnetic Resonance Imaging*, Vol. 5, No. 5, 1987, and "Vascular Morphology by Three-Dimensional Magnetic Resonance Imaging," by H. E. Cline et al., *Magnetic Resonance Imaging* Vol 7, pages 45-54, November, 1989.

Nuclear magnetic resonance (NMR) imaging is better at contrasting soft tissues than CAT x-ray scans, but suffers from the fact that there are many more soft tissue surfaces that are identified by any given threshold surface value, as compared to surfaces such as bone and organs. The difficulty with the connectivity algorithms of the prior art in situations where threshold surface values are close to each other is that they examine adjacent values in order to determine connectivity. This procedure inherently tends to bridge to tissues with similar data values even though the surfaces are not in fact connected. An additional drawback to such prior art techniques is the greatly increased amount of processing necessary to examine all of the adjacent values, increasing the delay in generating an image while at the same time producing images with poor surface discrimination. The problem becomes particularly acute for three-dimensional images of the human head where the large number of closely packed tissues exacerbate the surface discrimination difficulty.

A significant problem in displaying internal surfaces of closely packed tissues such as in the human head is, therefore, the need to segment the data samples into the various tissues. Such segmentation is preferably accomplished before an attempt is made to trace the surface of the tissue using a connectivity algorithm, so as to minimize the number of data points which must be investigated.

Accordingly, one object of the invention is to provide a system and method for displaying surfaces of internal structures within a body with good surface discrimination.

Another object is to provide a system and method for creating three-dimensional NMR images of structures within a human body without excessive delay in processing the data for generating the images.

Another object is to utilize echoes of the clinical pulse sequences of an NMR imaging system to form three-dimensional images of structures within a human body with good surface discrimination and without need for tedious manual editing.

SUMMARY OF THE INVENTION

In accordance with the illustrative embodiment of the present invention, statistical techniques are used to classify all of the data points into a plurality of tissue classes before surface generation of an internal structure is attempted. More particularly, a set of sample data points is selected so as to be distributed more or less uniformly over each of the tissues of interest. Such data points can be selected by viewing selected slices of data points and can be enhanced by displaying the intensities of two independent data sets against each other to produce clusters of data points corresponding to different tissue classes. The selected data points are then used to calculate a bivariate probability distribution, in the data space, of each of the tissue intensities. This probability distribution is then used to generate a feature map comprising an array of the most probable tissue identification labels for each point in the original data space. The feature map is used to segment the values in the original data set into the appropriate tissue classes. With two or more independent data sets available, the set providing the maximum contrast in intensity values can be chosen for subsequent processing of each tissue class into surface displays.

Once the data is segmented in accordance with the present invention, it can be smoothed to remove misclassified data points and to provide a smoothly varying surface normal vector to be used for gradient shading. Any known prior art connectivity algorithm can then be used to extract the surfaces of the identified tissues, confining the search to the segmented subset of tissue values. Color can be used to identify the different tissues and surface gradient shading can be used to improve the appearance of the three-dimensional display, all as is well known in the prior art.

BRIEF DESCRIPTION OF THE DRAWINGS

The features of the invention believed to be novel are set forth with particularity in the appended claims. The invention itself, however, both as to organization and method of operation, together with further objects and advantages thereof, may best be understood by reference to the following description taken in conjunction with the accompanying drawing(s) in which:

To facilitate reader understanding, identical reference numerals are used to designate elements common to the figures.

DETAILED DESCRIPTION

Figure 1:
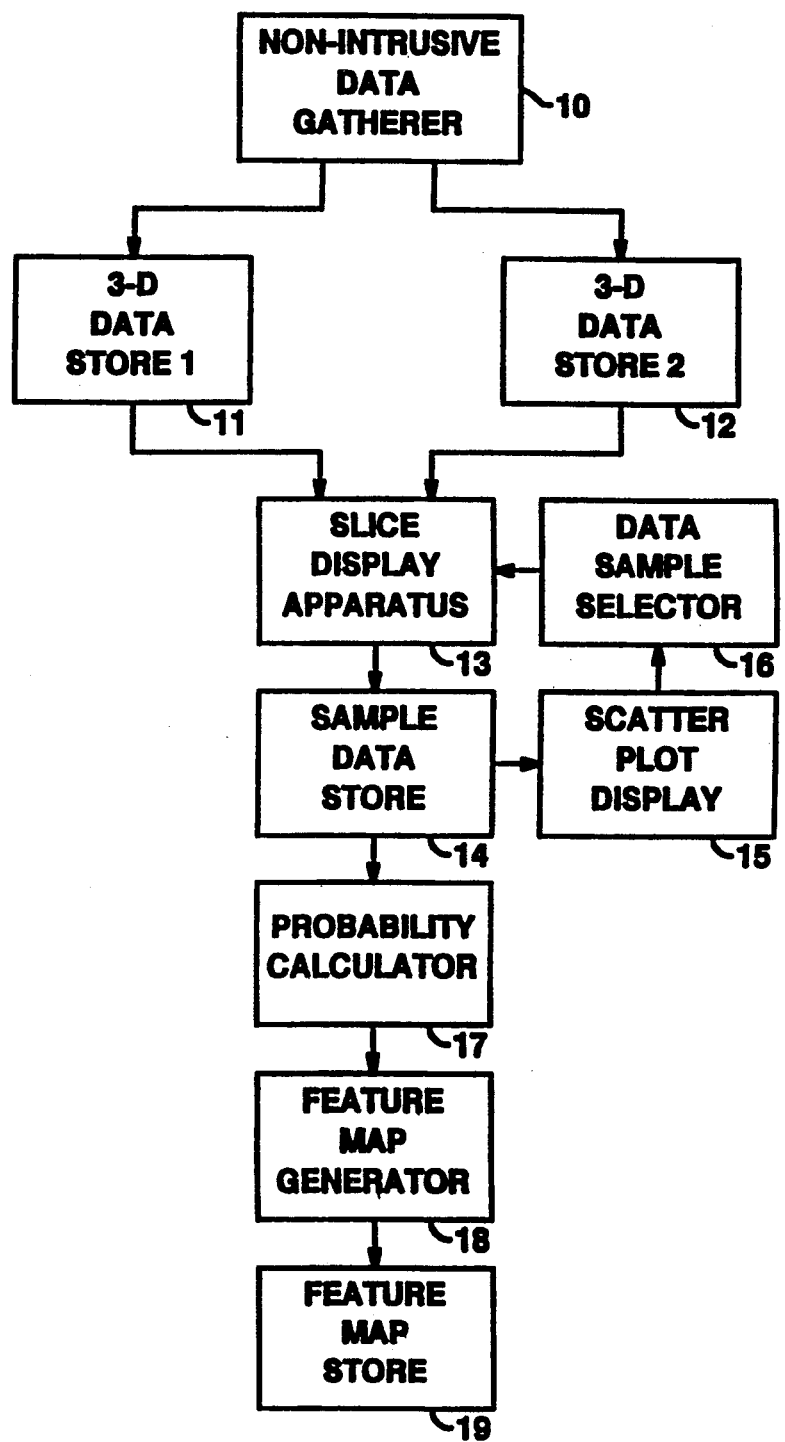
FIG. 1 is a block diagram of a data segmentation system in accordance with the present invention.

FIG. 1 is a block diagram of a data segmentation system in accordance with the present invention, comprising a non-intrusive data gatherer 10 such as an x-ray CAT scan apparatus, an NMR imaging device, or any other non-intrusive data gathering apparatus. The data segmentation techniques performed by this system produce a series of planar, grid-like arrays of values representing sections through a solid object such as the human anatomy. Since NMR techniques produce better data than CAT techniques for imaging soft tissues such as those within the human head, the preferred embodiment utilizes an NMR imaging device. Nuclear magnetic resonance scans conventionally produce two echoes from each point in the interior of the object. The first echo corresponds to the spin-spin relaxation at the scanned point while the second echo corresponds to the spin-lattice relaxation at the scanned point. As is well known, the magnitudes of the echo signals are proportional to the physical properties of the solid body and hence the gathered data represents such physical properties. Since NMR scanning produces two echoes for each point within the solid body, a first three-dimensional data storage device 11 is provided to store the first echo response from each scanned point while a second three-dimensional data storage device 12 is provided to store the second echo response from each scanned point. A slice display apparatus 13 is provided to selectively display the data from any planar slice of data in the data space in either of stores 11 and 12. Using a data sample selector 16, which may comprise, for example, a light pen or a touch-sensitive screen, sample data points are selected within each of a plurality of tissue classes displayed from a selected one of stores 11 and 12 on slice display apparatus 13. The displayed slices are chosen to provide the clearest differentiation between the various tissue classes, and the data points are selected to provide a uniform distribution of data samples over the volume of the tissues of interest. In the human head, for example, the tissue classes may comprise bone, brain, face, air, spinal fluid, brain fluid, arteries, veins, lesions and tumors, or any desired subset of these tissue classes.

Each data sample thus selected is paired with the corresponding data sample from the other one of data stores 11 and 12 and stored in a sample data store 14. When a significant number of such samples are assembled in sample data store 14, the data values for each stored pair of data samples are plotted against each other in a scatter plot display device 15. The displayed points in such a scatter plot tend to fall into clusters representing the different tissue classes. If each set of sample points is labeled with an identification of the tissue class from which it is selected, then the clusters of data points can be identified with the corresponding tissue class. Moreover, additional sample data points can be selected to provide a more uniform distribution of such sample data points over the tissues of interest, and to further specify those areas with an ambiguous tissue classification. Thus, iterative sequencing of the use of slice display apparatus 13, sample data store 14, scatter plot display 15 and data sample selector 16 permits the selection of a uniform distribution of sample points over all of the tissue classes of interest within a reasonable period of time. It has been found, for example, that an experienced user can obtain forty uniformly distributed sample data points for each of five different tissue classes in approximately five minutes.

Figure 3:
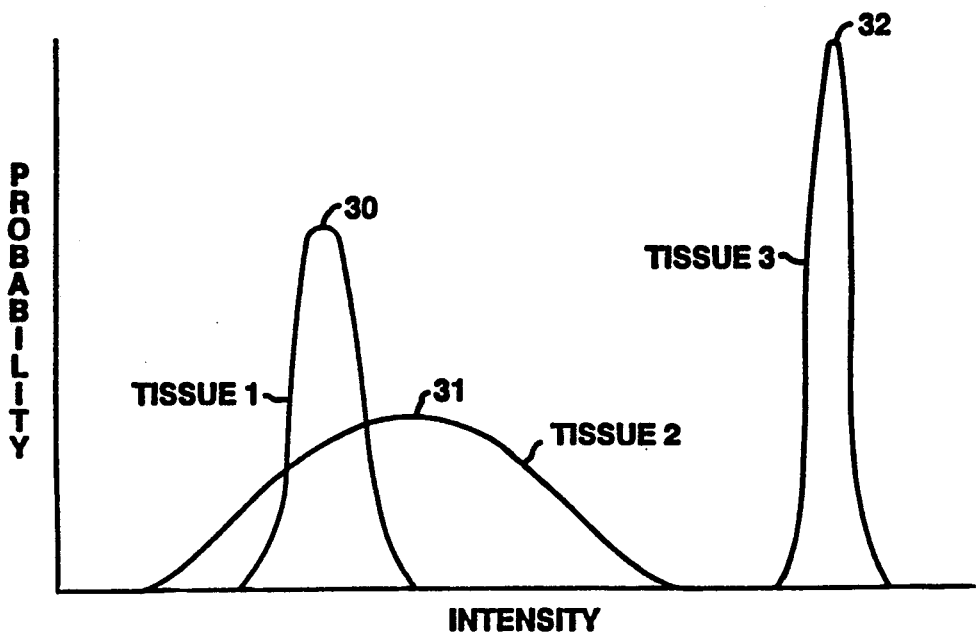
FIG. 3 is a typical two-dimensional, single variate probability distribution for each of three tissues of interest in a single slice of data from a non-intrusive data gathering system, useful in understanding the data segmentation system of the present invention.
Figure 4:
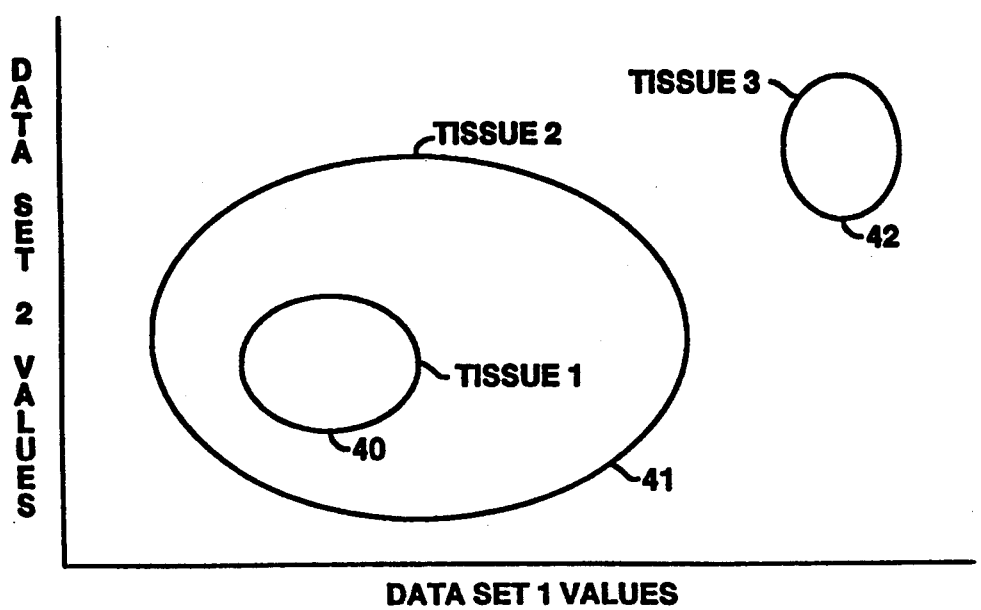
FIG. 4 is a typical scatter plot of a single slice of two independent data sets from a non-intrusive data gathering system showing the clustering of data points from different tissues and useful in selecting sample data points for the data segmentation process of the present invention.

Once an adequate number of sample point data pairs have been collected in sample data store 14, the sample point coordinates, intensity values and tissue identification are supplied to a probability calculator 17. Calculator 17 calculates a probability distribution for each tissue class across the entire data space. It is assumed that the recorded intensity values include random errors and that the position of each tissue in the data space follows a bivariate normal probability distribution. It is then possible to use the sample points to calculate the probability distribution for each tissue class, using the sample data points as representative of the various tissue classes. A typical two-dimensional, single variate probability distribution for three tissue classes is shown in FIG. 3, for illustrative purposes. A first tissue class 1 has a probability distribution overlapping the probability distribution for a second tissue class 2. A third tissue class 3 has a nonoverlapping probability distribution. Extending these probability distributions to three dimensions, and using bivariate probabilities, is straightforward. The corresponding scatter plot is shown in FIG. 4 where tissue data cluster 40 corresponds to probability 30 (FIG. 3), tissue data cluster 41 corresponds to probability 31 and tissue data cluster 42 corresponds to probability 32. It can be seen that identifying additional data points distributed throughout a tissue cluster is readily accomplished, using the scatter plots.

More specifically, for the two-fold data set of illustrative embodiment, the bivariate normal probability distribution can be represented by $f_i(x_1, x_2)$ where i is the tissue class identification, $x_1$ represents the data samples from the first echo data set for the ith tissue, from data store 11, and $x_2$ represents the data samples from the second echo data set for the ith tissue, from data store 12. The function $f_i$ depends on the deviates $X_1$ and $X_2$ of the sampled data values from the mean data values $<x_1>_i$ and $<x_x>_i$ for each data cluster representing a different tissue class. In accordance with standard statistical analysis, $$X_1 = x_1 - <x_1>_i \quad (1)$$
$$X_2 = x_2 - <x_2>_i$$

and the variances $\sigma_1$, $\sigma_2$ and the correlation $\rho$ are given by $$\sigma_1^2 = \frac{\Sigma X_1^2}{N} \quad (2)$$

$$\sigma_2^2 = \frac{\Sigma X_2^2}{N}$$

$$\rho \sigma_1 \sigma_2 = \frac{\Sigma X_1 X_2}{N}. \quad (3)$$

The probability distribution is then given by $$f_i(x_1, x_2) = \frac{e^{[-Q/2]}}{A} \quad (4)$$

where Q is a quadratic form in the deviates given by $$Q_i = \frac{1}{(1-\rho^2)} \left[ \frac{X_1^2}{\sigma_1^2} - \frac{2\rho X_1 X_2}{\sigma_1 \sigma_2} + \frac{X_2^2}{\sigma_2^2} \right]. \quad (5)$$

The amplitude A is chosen to make the total probability unity, i.e., $$A_i = 2\pi \sigma_1 \sigma_2 \sqrt{(1-\rho^2)}. \quad (6)$$

A bivariate normal distribution is a Gaussian with an elliptical cross section given by setting Q equal to a constant. The shape of the ellipse depends on the variances $\sigma_1$ and $\sigma_2$ and the correlation $\rho$. If the variables $x_1$ and $x_2$ are not correlated, the distribution function becomes a circular Gaussian in the sample space.

Any number n of three-dimensional data sets with different contrasts can be used to calculate a multivariant normal distribution by extending the probability function $f_i(x_1, \ldots, x_n)$ to the higher dimensions. The quadratic form $Q_i$ then becomes $$Q_i = \tfrac{1}{2} X'X^{-1}X \quad (7)$$

where X and X' are the n dimensional deviate vector and transpose vector and S is the covariance matrix with elements $$[S_{1m}] = \frac{\Sigma X_1 X_m}{N}. \quad (8)$$

The amplitude then becomes $$A_i = (2\pi)^{N/2} |S|^{\tfrac{1}{2}} \quad (9)$$

Increases in the number of data sets improve the tissue class segmentation and provide a richer set of alternative data values for surface calculations.

Once the probability calculation is completed for the sample data set in calculator 17 of FIG. 1, the probability distribution is passed on to a feature map generator 18. Generator 18 takes each possible data point in the available data space and uses the probability distributions for identifying the most likely tissue class for each data coordinate. These tissue class identifications for each data coordinate together comprise the feature map and are stored in a feature map store 19. More particularly, the feature map is calculated at each point in the sample space by identifying the tissue with the largest probability, as given by $$f_i(x_1, x_2) > f_j(x_1, x_2) \quad (10)$$

for all tissue classes j not equal to tissue class i. Consequently, the feature map is an array of the most probable tissue labels i at each point in the sample space. Substitution of the probability distribution from equation (4) into equation (10) and taking the natural logarithm, gives the relationship $$2\ln A_i + Q_i < 2\ln A_j + Q_j. \tag{11}$$

Equation (11) provides an easily applied classification algorithm which minimizes the total of the percentage errors of each tissue. It differs from Bayes' Rule in that each probability function is not weighted by the fraction of each tissue in the total volume. It is not possible, however, to use Bayes' Rule for classifying this three-dimensional data because the tissue volumes are not known before segmentation. It is therefore assumed that each tissue has an equal weight. The feature map thus generated can be used directly to segment the data in data stores 11 and 12 simply by attaching the tissue labels in store 19 to the data values in stores 11 and 12 for each of the corresponding coordinates.

Figure 2:
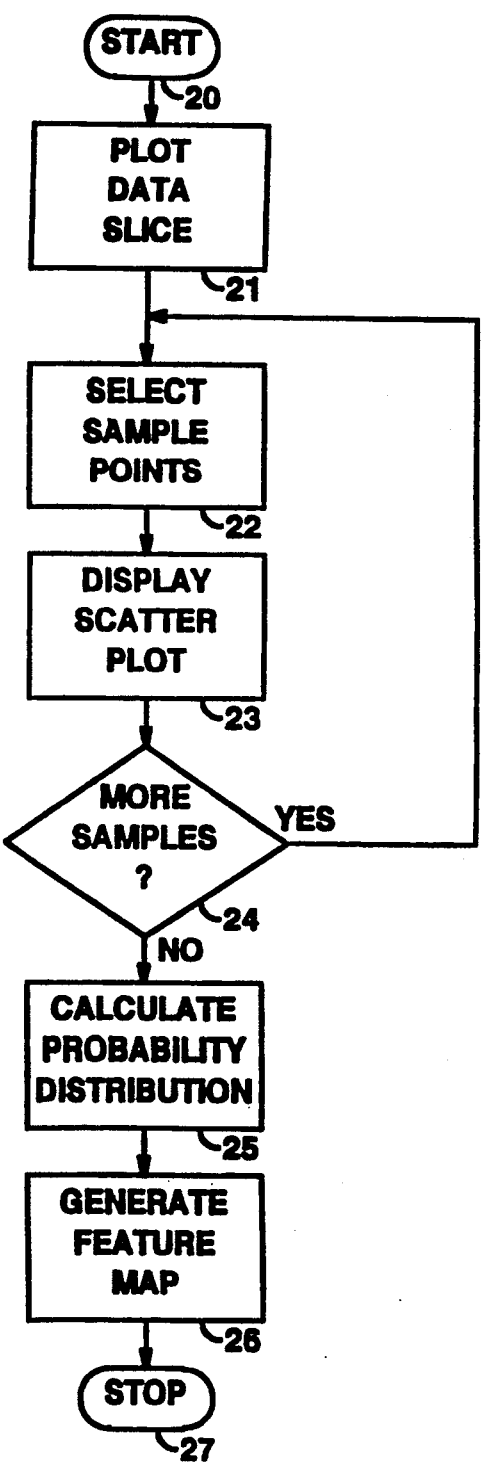
FIG. 2 is a flow chart of the steps of a data segmentation process practiced with the system of FIG. 1.

The segmentation system of FIG. 1 requires a minimum of intervention by the human user and produces a high quality feature map almost entirely automatically. The procedure for implementing data segmentation using the system of FIG. 1 is shown in FIG. 2, which is a flowchart of the data segmentation process using the system of FIG. 1. From a starting point 20, data slices are plotted at step 21. Using these data plots, the user selects sample data points at step 22 and displays the selected sample data points in a scatter plot at step 23. After viewing the displayed scatter plot, it is decided at decision step 24 whether any more samples are needed to discriminate all of the tissues of interest and to provide uniform sample distribution within the tissues of interest. If more samples are needed, step 22 is re-performed to select more sample data points and display the new scatter plot. If no more samples are needed, the bivariate probability distributions are calculated at step 25, using equation (4). Using the probability distributions from step 25, the feature map is generated at step 26, assigning the more probable tissue class to each coordinate of the data space. The process terminates at point 27 with the feature map available for further processing of the data to generate actual images.

Figure 5:
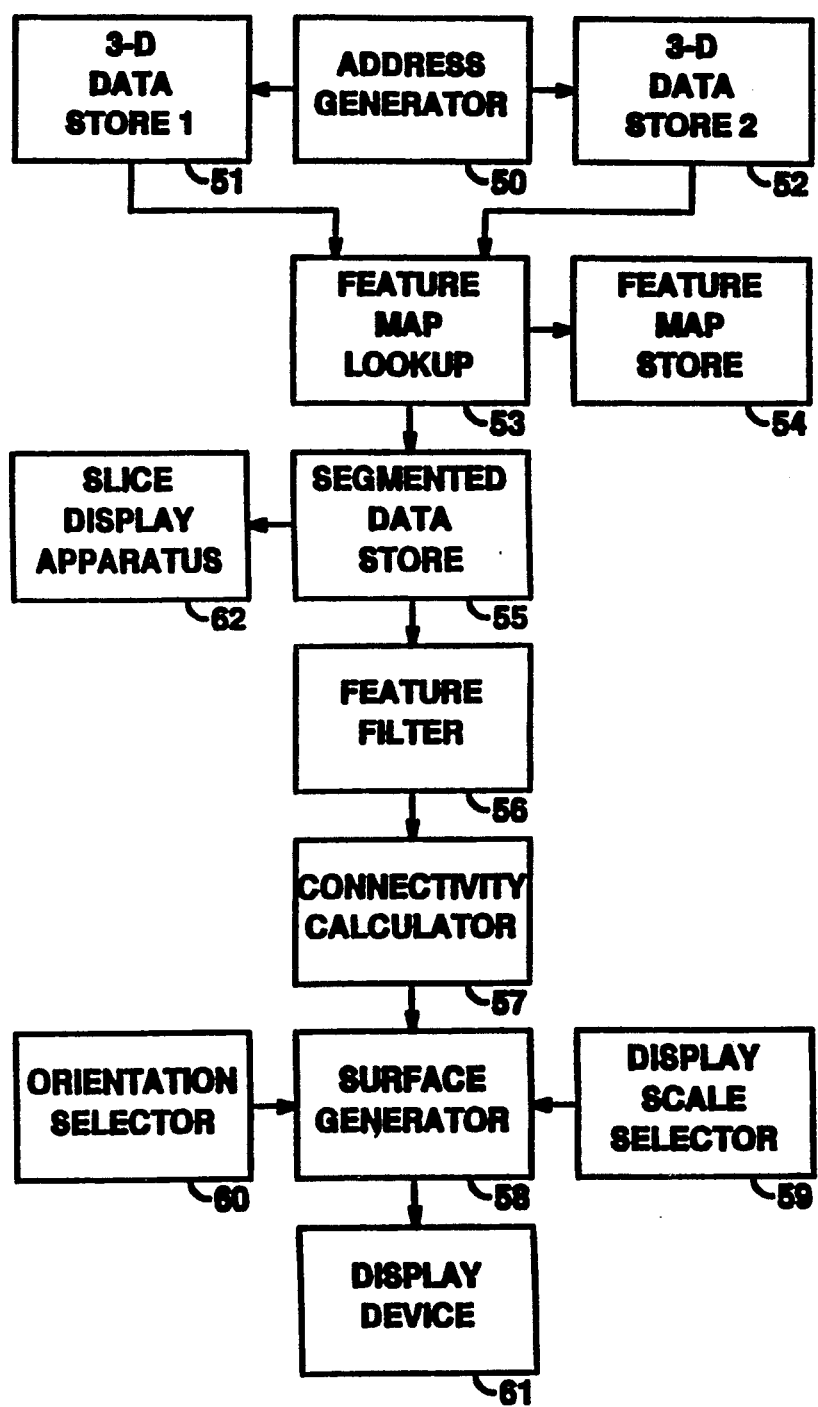
FIG. 5 is a general block diagram of an image processing system which can be used to generate images of three-dimensional surfaces from the data points segmented by the system of FIGS. 1 and 2.

Given an already calculated feature map from the process of FIG. 2, the data display system of FIG. 5 then processes the data to provide a display of the surfaces of the tissues of interest. More particularly, an address generator 50 simultaneously addresses two three-dimensional data stores 51 and 52 to gate out each data value at successive addresses. Using the feature map in a feature map store 54, a feature map lookup circuit 53 ascertains to which tissue class the current data value most likely belongs. An appropriate tissue identifier tag is associated with that data value and the augmented data stored in a segmented data store 55. In the final display, these tissue class identifier tags can be used to select a different color to be used to display the various tissues. It is possible to display and examine slices of the segmented data from segmented data store 55 in slice display apparatus 62, using the tissue identifier tag to color the various tissues. If the displayed tissue cross sections are of a uniform color, the original data was correctly sampled. Misclassified pixels, however, appear as regions of incorrect coloring, indicating that the original samples did not fully segment the data. The segmentation can be improved by adding some corrected sample points to the original set and recalculating the probability distributions in the system of FIG. 1.

The segmented data is subjected to filtering in a feature filter 56 to remove randomly misclassified data values and to smooth variations in the surface normal vector caused by poor definition of the direction of the surface of the segmented tissues. Such poor definition arises because the edges of the tissue regions are arbitrary step values generated by using only the low probability values at these edges. Filtering the segmented data is therefore used to both establish a smoothly varying surface normal vector to yield improved surface rendering and to remove the effect of isolated misclassified data points. A filter which is designed to approximate the three-dimensional diffusion equation is suitable for this purpose.

According to the three-dimensional diffusion equation, the concentration c of the ith tissue evolves with time according to the diffusion equation given by $$\frac{\partial c}{\partial t} = D\left[\frac{\partial^2}{\partial x} + \frac{\partial^2}{\partial y} + \frac{\partial^2}{\partial z}\right]c. \tag{12}$$

Initially, the concentration of the ith tissue is binary in the sense that each data point is either within or outside of the tissue. As time passes, the data points are allowed to move in accordance with the diffusion equation (12) and the sharp transition in the composition at the tissue surface becomes diffuse. If the aspect ratio a is the ratio between the slice thickness of the data and the size of the displayed pixel, then a $3 \times 3 \times 3$ diffusion filter, corrected for this aspect ratio, and after one iteration of the diffusion filter, is of the form $$c_{t+1} = \frac{c_t}{2} + \frac{a^2(c_{x+1} + c_{x-1} + c_{y+1} + c_{y-1}) + (c_{z+1} + c_{z-1})}{(4 + 8a^2)} \tag{13}$$

Diffusion filter equation (13) is applied only twice to the data so as to provide sufficient smoothing while not significantly degrading the resolution of the surfaces between tissues. Such smoothing removes isolated data values and reduces the effect of noise on the classification of tissues. As might be expected, there is a tradeoff between the improvement in segmentation and the loss of resolution generated by filtering. The filter can be applied twice without significant loss of resolution.

The filtered data from circuit 56 can be applied to any known connectivity calculator 57 such as that described in the aforementioned article entitled "High Resolution 3D Images of the Brain Using a Connectivity Algorithm," by H. E. Cline et al., published in *Magnetic Resonance Imaging*, Vol 5, No. 5, pages 345-352, 1987. Such a connectivity calculator starts with a given point in the tissue and constructs the surface by examining neighboring data values to trace and mark the surface data values. More particularly, the connectivity algorithm is recursive, starting with a seed point on the surface and collecting neighboring surface points which then become seeds for the next level of recursion. Only data points in the same tissue class need be examined, however, substantially reducing the amount of calculation while, at the same time, significantly improving surface discrimination. This recursive procedure continues until all of the connected data points for that tissue class are marked. A surface point intersects surfaces of equal concentration at the midpoint of the transition where the concentration c is equal to one-half. This connectivity algorithm can be used successively to select the surfaces of all of the tissues of interest for later display.

The data points defining the surface of interest can be constructed by using the so-called "dividing cubes" method taught in H. E. Cline et al. U.S. Pat. No. 4,719,585, granted Jan. 12, 1988, and described in "Two Algorithms for the Three-Dimensional Reconstruction of Tomograms," by H. E. Cline et al., *Medical Physics*, Vol. 15, No. 3, pages 320–327, May/June 1988. In this method, interpolation techniques are used between adjacent data samples to provide a data granularity matching the display pixel size. Interpolation techniques are also used to provide interpolated surface normal vectors for each interpolated surface point. A surface generator 58 provides a display list of the surface normal vectors for each of the surfaces of interest. These lists of surface normal vectors are supplied to a display device 61. An orientation selector 60 allows the user to select the viewing orientation while a display scale selector 59 allows the user to match the data to the available display pixel size, thus maximizing the display resolution. Display device 61 displays the various surfaces by coloring each tissue differently and shading each point on the surfaces by a weighting proportional to the surface gradient, or angular difference between the surface normal vector and the viewing angle, at each of the points on the surfaces. Hidden surfaces can be removed with a depth buffer as taught in the aforementioned copending application Ser. No. 275,154, filed Nov. 22, 1988, and assigned to applicants' assignee. Using standard graphic processing software, the surfaces can be selectively cut, rotated and translated to allow the user to view the surfaces in the most useful rendition. Such displays are typically used to plan surgery or to check on the progress of treatment.

While only certain preferred features of the invention have been illustrated and described herein, many modifications and changes will occur to those skilled in the art. It is, therefore, to be understood that the appended claims are intended to cover all such modifications and changes as fall within the true spirit of the invention.

What is claimed is:

1. A method for creating a segmented three-dimensional (3D) model of internal physical structures of a subject comprising the steps of:
    a) acquiring a first echo set of three-dimensional (3D) data values from a first spin echo from nuclear spins within a solid subject by non-intrusive data gathering means;
    b) acquiring a second echo set of three-dimensional (3D) data values from a second spin echo from nuclear spins within a solid subject by non-intrusive data gathering means;
    c) storing the first echo set;
    d) storing the second echo set;
    e) displaying an image showing physical structures of said subject to an operator created from one of the echo sets;
    f) selecting a plurality of locations of the image corresponding to the same tissue type, smaller in number than the data values in the echo sets and substantially uniformly distributed over a plurality of said physical structures;
    g) calculating spatial probability distributions on a scatter plot from the data values of the first and second echo sets corresponding to the selected locations of a plurality of said physical structures within said solid body for the selected tissue type and displaying the distributions,
    h) repeating steps "f" and "g" for a plurality of tissue types;
    i) utilizing the calculated probability distributions for assigning each of the data values of the first and second echo sets which had not been selected to a most probable one of the tissue types;
    j) spatially filter the assigned data values using digital means for the purpose of smoothing edges between data values assigned to different tissue types;
    k) determining connectivity among spatial regions of data values assigned to the same tissue type to create a plurality of 3D shapes of the same tissue type each being a different physical structure;
    l) displaying and manipulating the pluralities of 3D shapes of each tissue type on a display means to plan and guide a surgical procedure.

2. The method according to claim 1, wherein the probability distribution is calculated from the data values of the first and second echo sets according to the following equations:

$$f(x_1, x_2) = \frac{\exp\left(\frac{Q_i}{2}\right)}{A}$$

where $x_1$ and $x_2$ are the sampled values; A is a constant chosen to make the total probability unity, $$Q_i = \frac{1}{(1-\rho^2)}\left[\frac{X_1^2}{\sigma_1^2} - \frac{2\rho X_1 X_2}{\sigma_1 \sigma_2} + \frac{X_2^2}{\sigma_2^2}\right]$$

$$X_1 = x_1 - <x_1>_i \quad X_2 = x_2 - <x_2>_i$$

$<x_1>_i, <x_2>_i$ are the ith means data values, $$\sigma_1^2 = \frac{\Sigma X_1^2}{N} \quad \sigma_2^2 = \frac{\Sigma X_2^2}{N}$$

N is the number of sample points, and $$\rho = \frac{\Sigma X_1 X_2}{N \sigma_1 \sigma_2}.$$

3. The method according to claim 1, wherein the first echo set of three-dimensional (3D) data values is acquired by nuclear magnetic resonance imaging.

4. A system for displaying two-dimensional images of internal structures of three-dimensional solid bodies, said system comprising:
    a three-dimensional (3D) data store means adapted for storing at least two three-dimensional data sets representing the values of two different physical properties associated with said three-dimensional body at regularly spaced grid locations within said body;
    b) a data sample selector adapted for selecting a plurality of values from one of the three-dimensional data sets, each of the values being identified with a particular one of said internal structures of a particular tissue type;

c) a probability calculator adapted for calculating a spatial probability distribution from the selected values, and plotting the distribution on a scatter plot diagram;

d) a feature map generator adapted for assigning all of the values of the three-dimensional data set to a unique one of the tissue types depending on a maximum value of the calculated probability distribution;

e) a connectivity calculator for identifying internal structures by grouping data values corresponding to contiguous locations within said three-dimensional solid body being assigned to the same tissue type by a connectivity algorithm; and f) display means for displaying surfaces of desired internal structures.

5. The display system according to claim 4, further comprising nuclear magnetic resonance means for gathering said three-dimensional data sets.

6. The display system according to claim 4, further comprising filter means for re-assigning the values of the three-dimensional data set for values corresponding to locations on a boundary of adjacent internal structures to smooth each of the structures.

7. The display system according to claim 4, further comprising an orientation selector adapted for selecting the viewing angle for viewing said displayed surfaces of the desired internal structures.

8. The display system according to claim 4, further comprising means for selecting a resolution of the displayed images to match the resolution capability of said means for displaying.

9. The display system according to claim 4, further comprising means for utilizing a different color to display the surface of each of the desired internal structures.

10. The display system according to claim 4, further comprising means for shading each point on the surfaces by an intensity proportional to a direction of a surface gradient at said each point.

11. A segmentation system for creating three-dimensional (3D) models by classifying magnetic resonance imaging (MRI) data into stationary tissue and flowing fluid types comprising:

a) a magnetic resonance scanner adapted for obtaining a three dimensional (3D) first echo set and a 3D second echo set each having a plurality of entries, with each entry corresponding to a three-dimensional location (x,y,z) of a subject and each echo set representing a plurality of tissue types within the subject;

b) an slice display apparatus adapted for creating an image from the first and second echo sets, and adapted for creating a scatter plot diagram;

c) data sample selector adapted for allowing an operator to select a desired types of tissue and a location (x,y) on the image;

d) a sample data store unit adapted for storing a classification value indicating the selected tissue type a data value of the first echo set and a data value from the second echo set for each selected array element location, the classification value being plotted to obtain the scatter plot;

e) probability calculator adapted for synthesizing classification values for data values of the first echo and second echo sets having no classification value, the synthesized values pertaining to a most probable tissue type;

f) feature map store adapted for storing a spatial representation of tissue types;

g) a feature map generator adapted for creating a feature map being a spatial representation of classification values from information stored in the sample data store unit and the synthesized classification values and storing it in the feature map store, and adapted for classifying remaining entries in the feature map according to most probable tissue type;

h) a segmented data store unit coupled to the feature map generator adapted for storing the classified entries from the feature map lookup; and i) a three-dimensional processor for producing a three-dimensional model from the classification values at all array element locations.

12. The segmentation system of claim 11 wherein the three-dimensional processor comprises:

i1) feature map lookup adapted for looking up the classification values of tissue types in the feature map store for desired locations;

i2) a feature filter adapted for digitally smoothing a number of transitions between adjacent tissue classifications;

i3) a connectivity calculator adapted for identifying contiguous locations having the same classification values indicating the same tissue type starting from selected locations;

i4) an orientation selector adapted for interacting with the operator and defining a desired model orientation;

i5) a display scale selector adapted for interacting with the operator and defining a desired model size;

i6) a surface generator responsive to the orientation selector and the display scale selector adapted for creating a signal indicating a three dimensional surface of a desired size oriented in a desired orientation of physical structures;

i7) a display device adapted for receiving the signal from the surface generator and a 3D image representing said physical structures of said subject.

* * * * *